(12) United States Patent
Wold

(10) Patent No.: US 6,754,543 B1
(45) Date of Patent: Jun. 22, 2004

(54) METHOD AND ARRANGEMENT FOR CALIBRATION OF INPUT DATA

(75) Inventor: Svante Wold, Vännäs (SE)

(73) Assignee: Umetri Aktiebolag, Umea (SE)

( * ) Notice: Subject to any disclaimer, the term of this patent is extended or adjusted under 35 U.S.C. 154(b) by 0 days.

(21) Appl. No.: 09/720,425
(22) PCT Filed: Jul. 11, 1999
(86) PCT No.: PCT/SE99/01035
§ 371 (c)(1), (2), (4) Date: Mar. 14, 2001
(87) PCT Pub. No.: WO99/67722
PCT Pub. Date: Dec. 29, 1999

(30) Foreign Application Priority Data

Jun. 22, 1998 (SE) ............................................. 9802229

(51) Int. Cl.[7] ........................ G06F 17/16; G06F 17/40; G05F 13/00
(52) U.S. Cl. ........................... 700/52; 702/190; 700/54; 700/29; 700/73
(58) Field of Search ................................ 356/451, 300; 702/90, 190; 703/11; 700/55, 54, 52, 73, 29; 708/801, 814

(56) References Cited

U.S. PATENT DOCUMENTS

| | | | | |
|---|---|---|---|---|
| 5,243,546 A | * | 9/1993 | Maggard | 702/90 |
| 5,379,238 A | * | 1/1995 | Stark | 703/11 |
| 5,459,677 A | * | 10/1995 | Kowalski et al. | 703/2 |
| 5,498,875 A | * | 3/1996 | Obremski et al. | 250/458.1 |
| 5,568,400 A | * | 10/1996 | Stark et al. | 702/85 |
| 5,592,402 A | * | 1/1997 | Beebe et al. | 703/6 |
| 5,606,164 A | * | 2/1997 | Price et al. | 250/339.09 |
| 5,750,994 A | * | 5/1998 | Schlager | 250/339.11 |
| 5,991,653 A | * | 11/1999 | Richards-Kortum et al. | 600/475 |

FOREIGN PATENT DOCUMENTS

EP 0 581 023 2/1994

OTHER PUBLICATIONS

Hrushcka, W.R. and Norris, K. (1982) "Least squares curve fitting of near infrared spectra predicts protein and moisture conten of ground wheat." Applied Spectroscopy, vol. 36, p. 261–265.*
Kvalheim, O.M. (1988) "A partial least squares approach to inerpretative analysis of multivariate data." Chemometrics and Intelligent Laboratory Systems, vol. 3, p. 189–197.*
Kvalheim, O.M. (1987) "Latent structure decompositions (projections of multivariate data." Chemometrics and Intelligent Laboratory Systems, vol. 2, p. 283–290.*
Ottestad, P. (1975) "Component analysis. An Alternate System." Int. Stat. Rev., vol. 43, p. 83–108.*
H. Martens and T. Naes, "Multivariate Calibration," Wiley, N.Y., 1989.*
A. Hoskuldsson, "PLS Regression Methods," J. Chemometrics, vol. 2, p. 211–228, 1998.*

* cited by examiner

Primary Examiner—Ramesh Patel
Assistant Examiner—Aaron Perez Daple
(74) Attorney, Agent, or Firm—Pillsbury Winthrop LLP

(57) ABSTRACT

NIR spectra are often pre-processed in order to remove systematic noise such as base-line varation and multiplicative scauer effects. This is done by differentiating the spectra to first or second derivatives, by Mtltiplicative Siga Correction (MSC), or by sirnilar filtering methods. This pre-processinp may, however, also remove infosmaion fror The spectra regarding Y (the measured response variable in multivarate calibration applications). Provided is a variant ofPLS that can be used to achieve a signal correction that is as close to orthogonal as possible to a given Y-vector or Y-matrix (430). Thus, ensung that the signal correction removes as little information as possible regarding Y. In the case when the number of X-variables, in an X matrix, K exceeds the number of observations N, strict orthogonality is obtined. A filter (470) according to the present invention is named Orthogonal Signal Correction (OSC).

10 Claims, 8 Drawing Sheets

METHOD AND ARRANGEMENT FOR CALIBRATION OF INPUT DATA

TECHNICAL FIELD

The present invention pertains to a method for concentration or property calibration of substances or matter and an arrangement for calibration of spectroscopic input data from samples, whereby concentration or property calibration determines a model for further samples from the same type.

BACKGROUND OF THE INVENTION

Near-infrared (NIR) spectroscopy is being increasingly used for the characterization of solid, semi-solid, fluid and vapor samples. Frequently the objective with this characterization is to determine the value of one or several concentrations in the samples. Multivariate calibration is then used to develop a quantitative relation between the digitized spectra, a matrix X, and the concentrations, in a matrix Y, as reviewed by H. Martens and T. Naes, Multivariate Calibration. Wiley, N.Y., 1989. NIR spectroscopy is also increasingly used to infer other properties Y of samples than concentrations, e.g., the strength and viscosity of polymers, the thickness of a tablet coating, and the octane number of gasoline.

The first step of a multivariate calibration based on NIR spectra is often to pre-process the data. The reason is that NIR spectra often contain systematic variation that is unrelated to the responses Y. For solid samples this systematic variation is due to, among others, light scattering and differences in spectroscopic path length, and may often constitute the major part of the variation of the sample spectra. Another reason for systematic but unwanted variation in the sample spectra may be that the analyte of interest absorbs only in small parts of the spectral region. The variation in X that is unrelated to Y may disturb the multivariate modelling and cause imprecise predictions for new samples.

For removal of undesirable systematic variation in the data, two types of pre-processing are commonly reported in the analytical chemistry literature, differentiation and signal correction. Popular approaches of signal correction include Savitzky-Golay smoothing by A. Savitzky and M. J. E. Golay, Anal. Chem. 65, 3279–3289 (1993), multiple signal correction (MSC) H. Martens and T. Naes, Multivariate Calibration. Wiley, N.Y., 1989 and P. Geladi, D. MacDougall, and H. Martens, Linearization and Scatter-Correction for Near-Infrared Reflectance Spectra of Meat, Applied Spectroscopy, 3 (1985), 491–50, Fourier transformation by P. C. Williams and K. Norris, Near-Infrared Technology in Agricultural and Food Industries, American Cereal Association, St. Paul, Minn. (1987), principal components analysis (PCA) by J. Sun, Statistical Analysis of NIR data: Data pretreatment. J.Chemom. 11 (1997) 525–532, variable selection H. Martens and T. Naes, Multivariate Calibration. Wiley, N.Y., 1989 and M. Baroni, S. Clementi, G. Cruciani, G. Constantino, and D. Riganelli. Predictive abilityof regression models, Part 2: Selection of the best predictive PLS model. J. Chemom. 6 (1992) 347–56, and base line correction H. Martens and T. Naes, Multivariate Calibration. Wiley, N.Y., 1989 and R. J. Barnes, M. S. Dhanoa, and S. J. Lister. Standard Normal Variate Transformation and De-trending of Near-Infrared Diffuse Reflectance Spectra Appl.Spectrosc. 43 (1989) 772–777.

These signal corrections are different cases of filtering, where a signal (e.g., a NIR spectrum) is made to have "better properties" by passing it through a filter. The objectives of filtering often are rather vague; it is not always easy to specify what is meant by "better properties". Even, in the case of calibration, where it is possible to specify this objective in terms of lowered prediction errors or simpler calibration models, it is difficult to construct general filters that indeed improve these properties of the data.

SUMMARY OF THE DISCLOSED INVENTION

The present invention relates to a method and an arrangement that removes irrelevant parts from an input data set X of samples from substances or matter such as infrared and near-infrared spectroscopic input data, other spectroscopic input data, input data for predictions and generally for input data which can be categorized in sets or matrixes according to the present invention. This is achieved through ensuring that the removed part is orthogonal to Y, or as close to orthogonal as possible. The approach according to the present invention has been named OSC (Orthogonal Signal Correction).

Hence, the present invention provides a method for pretreatment (filtering) of input data from samples of substances or matter collected with the purpose of concentration or property calibration. A calibration determines a filter model for further samples of the same type, comprising the steps of:

optionally transform, center, and scale the input data to provide two start sets. arranging said input data in an input set;

determining a concentration or property set;

determining a score set and a loading set and their product, said product resembling the input set as much as possible under the constraint that the score set is orthogonal to the concentration or property set;

filtering said input data by subtracting said product from the input set in order to remove variations relating to properties other than present calibration properties; whereby said model determines the filtering, thus providing that further samples, from the same type of samples, can be filtered with the filter model.

In one embodiment sets are arranged as two matrixes or one matrix and one concentration or property vector.

In another embodiment the bilinear filtering is combined with a linear filtering method. The another embodiment filtering method is one of wavelet-filtering or Fourier-filtering in a preferred embodiment.

In yet another embodiment the model is improved by applying multiple sets of input data as training sets and repeating said steps with a better concentration or property, thus tuning the filtering model.

Further provided by the present invention is an arrangement for concentration or property calibration of samples from spectroscopic input data. The concentration or property calibration determines a filter means for further samples of the same type, comprising:

transforming means, centering means, and scale means to optionally operate on the input data in order to provide two start sets.

arrangement means for arranging said input data in an input set;

determining means for determining a concentration or property calibration set, a score set and a loading set;

multiplication means for determining the product between the score set and the loading set, said product resembling the input set as much as possible under the constraint that the score set is orthogonal to the concentration or property set;

filter means for filtering said input data by subtracting said product from the input set in order to remove variations relating to properties other than present calibration properties; whereby said model determines the filtering, thus providing that further samples of the same type can be filtered with the filter model.

In one embodiment of said arrangement, the sets are arranged as two matrixes or one matrix and one concentration or property vector.

In another embodiment said bilinear filtering is combined with filtering through another linear filtering means. Said another filtering means is one that, for example, provides wavelet-filtering or Fourier-filtering.

In yet another embodiment said filter model is improved by applying multiple sets of input data as training sets to said means, thus providing better determined properties by tuning the filtering model.

BRIEF DESCRIPTION OF THE DRAWINGS

For a more complete understanding of the present invention and for fuirther objectives and advantages thereof, reference may now be had to the following description taken in conjunction with the accompanying drawings, in which.

PREFERRED EMBODIMENTS OF THE INVENTION

The present invention is henceforth described as using input data from near-infrared or infrared spectroscopy, but it should be appreciated that it is possible to enter input data from almost any technical field as long as the objectives set forth through the invention are fulfilled. Hence, the method according to the present invention is not limited to spectroscopic inpuLt data. Other possible technical fields presenting input data are e.g. relating to predictions, forecasts etc. Also, the term property used in the present invention shall be given a broad interpretation comprising such properties of solid, semi-solid, fluid, vapour, samples etc, as, concentration, density, elasticity, viscosity, strength, thickness, class belonging (e.g. octane number for petrol classification) etc and predictions from probability input (e.g. stock market information) or other input figures for prediction from any technical field etc.

As an illustration, a modeling of the viscosity of three sets of modified cellulose samples in termns of their MIR reflectance spectra and a similar example where NIR spectra are used to model and predict 17 measured properties of pulp samples is displayed in the present description.

In the present description of a preferred embodiment capital bold characters are used for matrixes, e.g., X and Y, small bold characters for column vectors, e.g., v, non-bold characters for vector and matrix elements, e.g., $x_{ik}$, and $v_i$, and for indices, e.g., i, j, k, and l, and capital non-bold characters for index limits, e.g., K and N, and A. Row vectors are seen as transposed vectors, e.g., v', and hence transponation is indicated by a prime '. The index i is used as sample index (rows in X and Y; i=1,2, . . . , N) and the index k as index of X-variables (k=1,2, . . . , K).

Figure 1:
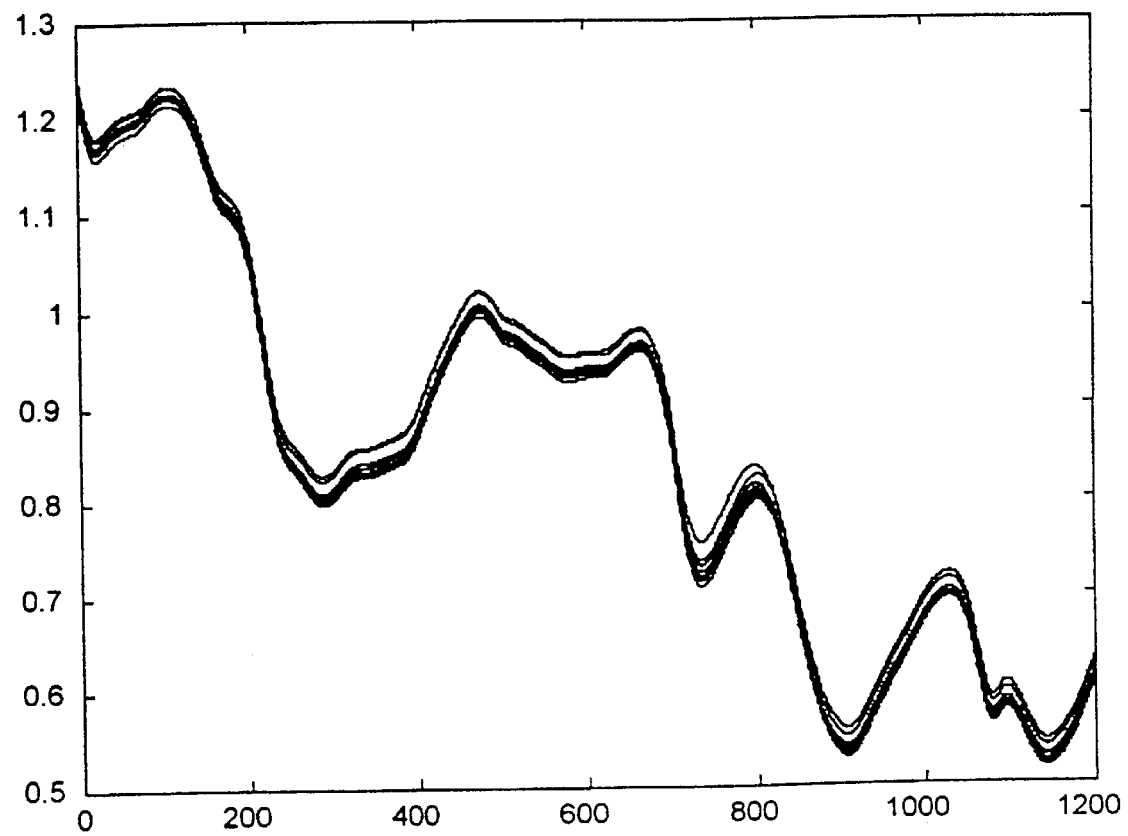
FIG. 1 illustrates a raw near-infrared (NIR) reflectance spectra.

Earlier, before the use of multivariate calibration, the unanimous agreement was that ideal spectra looked like well resolved NMR (Nuclear Magnetic Resonance) or IR spectra, i.e., mainly a straight baseline plus some narrow and symmetrical peaks unambiguously raising above this baseline. As depicted in FIG. 1, near-infrared (NIR) reflectance spectra do not have this appearance. On the contrary, there are baseline and other variations which are variations or measurement errors arising from measurement instruments and variations due to a change of components that contribute sample variations but are not related to variables of interest (irrelevant information).

In FIG. 1 the horizontal scale comprises spectroskopical variable numbers from 1 to 1201 (including 0) which originate from 1201 digitized values. The vertical scale depicts the spectral amplitude in arbitrary units.

Noise introduces "wiggles", but could be removed by a judicious "filtering" of the spectra. Much of the objectives of filtering are still formulated accordingly, as a way to make signals and spectra "smooth" and pleasing for the eye, and thus easy to interpret.

Figure 2:
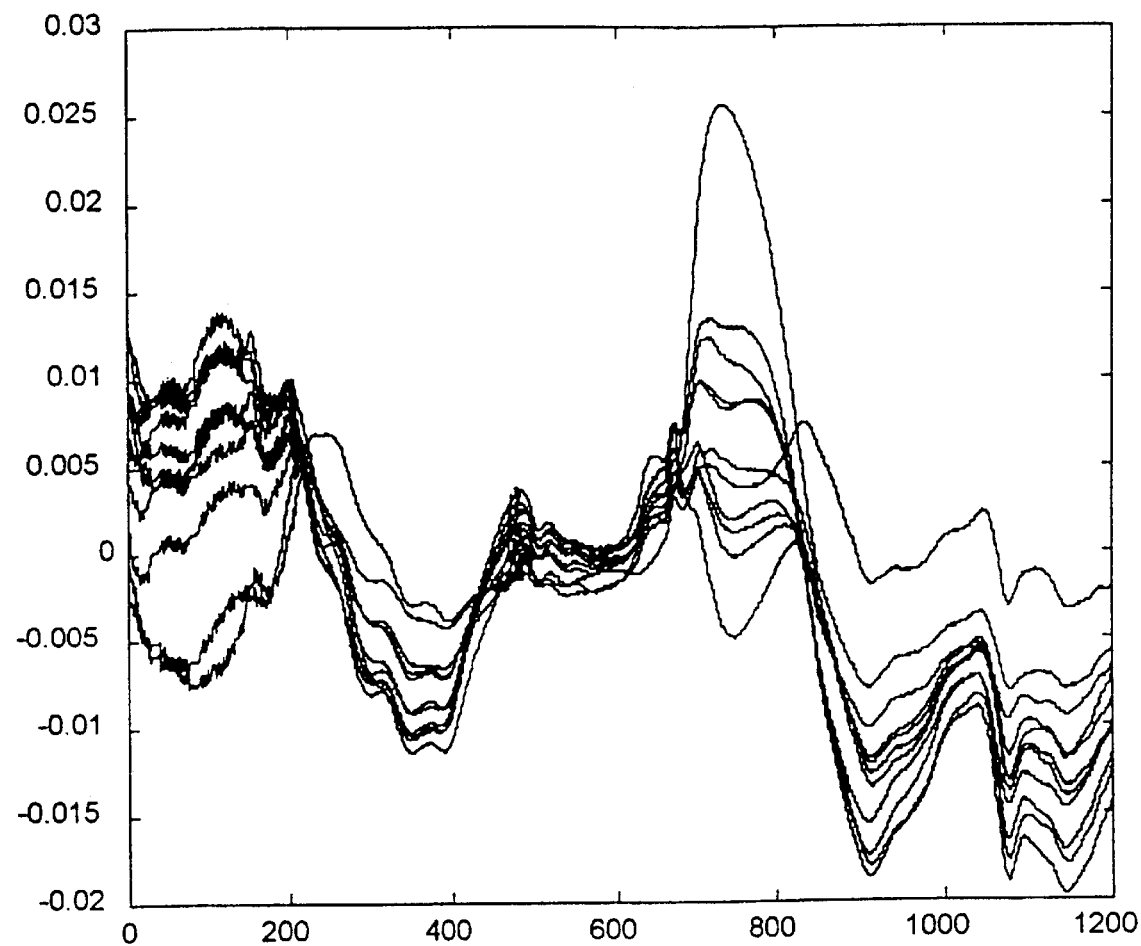
FIG. 2 illustrates corrected (OSC) near-infrared (NIR) reflectance spectra according to the present invention.

With multivariate analysis, however, a spectra is evaluated by computer means. There is not much evidence that "smooth" and eye-pleasing signals contain more information for computerized filtered approaches than do rough unfiltered spectra as illustrated according to the reflectance spectra depicted in FIG. 2. Where FIG. 2 is a corrected (OSC) near-infrared (NIR) reflectance spectra according to the present invention. The scales in FIG. 2 are in accordance with the FIG. 1 scales.

In essence, in order to construct an efficient filtering approach, there is a need to quantitatively formulate criteria for what the filtering is supposed to achieve. In multivariate calibration, it is quantitatively specified at least one objective of filtering, namely that the filtering should not remove information about Y from the spectra X. Here Y is what is calibrated against, i.e., analyte concentrations or other sample "properties". This "non-removing" can be stringently formulated, namely that the information in Y should be unrelated, orthogonal, to what is removed from X by the filtering.

To achieve such orthogonality, however, filters have to be expressed in such a way that their orthogonality to a vector or matrix, Y, can be quantified. This seems easiest accomplished by expressing the filtering as removing a bilinear structure from X, i.e., a product of a "score" matrix, T, times a loading matrix, P'. Orthogonal to Y then means that both T'Y and Y'T are matrixes with only zero-valued elements.

As discussed by Sun in J. Sun, Statistical Analysis of NIR data: Data pretreatment. J. Chemom. 11 (1997) 525–532, it is possible to formulate a class of filters as PCA-like multivariate projections. Here PCA means principal components analysis as further described in J. E. Jackson. A User's guide to principal components. Wiley, N.Y., 1991. Basing a filter on unmodified PCA has the advantage that a PC model would describe as much as possible of X, and hence should catch most systematic variation in X. However, the drawback is that this systematic variation contains both the one that is linearly unrelated to Y, and the one that contains linear information about Y.

PCA-like (Principal Components Analysis) filters can be written as:

$$X = TP' + E$$

Here X denotes the (N×K) matrix of unfiltered, uncorrected, set of digitised spectra, and E is the (N×K) matrix of "filtered" spectra. The (N×A) score matrix is denoted by T, and P' is a (K×A) matrix of "filters", loadings. The numbers of samples and variables of the "training set" (calibration set) are N and K, and A is the number of components. Sun has found A=1 or 2 to be optimal in the cases he has reported J. Sun, Statistical Analysis of NIR data: Data pretreatment. J. Chemom. 11 (1997) 525–532.

Thus, if T can be made orthogonal against Y, information is not removed from X that is linearly related to Y. With this insight, it is possible to develop filters, base line corrections, etc., with an orthogonal constraint.

Considering often used Additive and Multiplicative Signal Correction (MSC), by P. Geladi, D. MacDougall, and H. Martens, Linearization and Scatter-Correction for Near-Infrared Reflectance Spectra of Meat, Applied Spectroscopy, 3 (1985), 491–50, see also H. Martens and T. Naes, Multivariate Calibration. Wiley, N.Y., 1989. Here each digitized spectrum, the row vector $x_i'$, is "normalised" by regressing it against the average spectrum of the training set, m:

$$x_{ik} = a_i + b_i m_k + e_{ik}$$

The average training set spectrum has the elements:

$$m_k = \Sigma x_{ik}/N$$

Then, from each row, $x_i'$, subtract the intercept ($a_i$) and divide by the multiplicative constant ($b_i$):

$$X_{i, corr}' = (x_i' - a_i)/b_i$$

It is noticed that this correction (filter) can not be expressed as a bilinear, PCA-like, expansion. Hence, the MSC -can not in a simple way be orthogonalized against Y. Also realizing that there is a substantial risk that the vectors a and b are correlated to Y, and hence that MSC may remove from X information related to Y.

The same argument applies to the standard normal variate (SNV) correction of Barnes et al, see R. J. Barnes, M. S. Dhanoa, and S. J. Lister. Standard Normal Variate Transformation and De-trending of Near-Infrared Diffuse Reflectance Spectra. Appl. Spectrosc. 43 (1989) 772–777. This filter has exactly the same mathematical form as the one of MSC, but the parameters aj and b are determined as the average and the standard deviation of the i:th row of X, respectively.

However, if the sample spectra are fairly similar to their mean, and if the "slopes" $b_i$ are not too far from 1.0 or otherwise fairly constant, a two component bilinear expansion can still fairly well approximate the above corrections. Then OSC as described below would accomplish a filtering similar to MSC and SNV, but without removing relevant information from X according to the present invention.

In accordance with the present invention it is now possible to remove bilinear components from X which are orthogonal to Y, i.e. make a signal correction that does not remove information from X. This is done by setting up a PCA/PLS-related solution which removes only so much of X as is unrelated (orthogonal) to Y. This approach is based on the fact that as long as steps of NIPALS iterative algorithm of the classical two-block PLS regression are retained, the weight vector w can be modified in any way to encompass constraints, smoothness, or, as here, the objective that t=Xw is orthogonal to Y. This fact was shown by A. Höslkuldsson, PLS regression methods. J. Chemometrics 2 (1988) 211–228. Hence, the OSC algorithm will be identical to the ordinary PLS algorithm except for the crucial step of determining the weights, w. Normally, these are determined as to maximize the covariance between X and Y, herein they are determined as to minimize this covariance, i.e., to get as close to orthogonality between t and Y as possible. Essential features of the OSC method are:

(a) that the signal correction (filtering) is expressed as the subtraction of a bilinear, PLS-like, expression, T P' ; and (b) that the "OSC scores", $t_a$, can be determined from new sample spectra as $$t_{new,a} = x_{new} w_a.$$

When the number of X-variables, K, is larger than N (the number of training samples), it is always possible to find an exactly orthogonal OSC solution, but if K<N this is not always possible. This also means that for K>N, there are infinitely many OSC solutions, where a model according to the present invention is set up to find the one that models as much of X as possible by each component, i.e., each product of the score vector $t_a$ and the loading vector $p_a$. This solution may not always be the "best", however, and additional constraints on the OSC w vectors may be warranted.

Below an explanation of the present version of the OSC method is given.

1. Optionally transform, center, and scale the data to provide a "raw" matrix X and Y.
2. Start by determining the first principal component of X, with the score vector, t.
3. Orthogonalize t to Y.

$$t_{new} = (1 - Y(Y'Y)^{-1}Y')t$$

4. Determine a weight vector, w, that makes $Xw = t_{new}$. This is done by a PLS estimation giving a generalised inverse= $X^-$ $$w = X^- t_{new}$$

5. Determine a new score vector from X and w $$t = Xw$$

6. Calculate an updated loading vector $$p' = t'X/t't$$

7. Check for convergence, by testing if t has stabilized

Convergence if $\|t - t_{old}\|/\|t\| < 10^{-6}$ if not convergence, return to step 3, otherwise continue to step 8.

8. Subtract the "correction" from X, to give residuals, E $$E = X - tp'$$

9. Continue with the next "component" using E as X, then another one, etc., until satisfaction.

An important remark is that if too many OSC components are subtracted from the original X matrix, it will end up with a MLR (Multiple Linear Regression) solution since all information not correlated to Y then has been removed. Using only two or three components for the filtering will not, however, result in problems of that kind.

10. New samples (the prediction set) are corrected using W and P of the calibration model. For each new observation vector, $x_{new}'$:

$$t_1 = x_{new}' w_1$$

$$e_1' = x_{new}' - t_1 p_1'$$

$$t_2 = e_1' w_2$$

$$e_2' = e_1' - t_2 p_2'$$

and so on! After A components, the final residuals are the corrected x-data, which then give the predicted values of $y_{new}'$ (predicted response values for the new sample).

Before the determinations, X and Y can be transformed, centered and scaled as discussed further below.

One embodiment of OSC according to the present invention determines and removes from X one component at a time according to the standard NIPALS (Non Linear iterative Partial Least Square) method. This has the advantage to make the approach work also with missing data in the same way as ordinary PLS and PCA.

PLS, meaning partial least squares projection to latent structures, is a particular method for multivariate calibration where a model is developed for the relation between a matrix of input data, X, and a vector or matrix of concentration or property data, Y, as described in S. Wold, A. Ruhe, H. Wold and W. J. Dunn III, The Collinearity Problem in Linear Regression. The Partial Least Squares Approach to Generalized Inverses, SIAM J. Sci. Stat. Comput. 5 (1984) 735–743, and in S. Wold, H.Martens, and H. Wold. The multivariate calibration method in chemistry solved by the PLS method. In Proc.Conf.Matrix Pencils (A. Ruhe and B. Kågström, ed.s). Lecture notes in mathematics. Springer Verlag, Heidelberg, 1983, pp. 286–293, and in H. Martens and T. Naes, Multivariate Calibration. Wiley, N.Y., 1989.

The first step in determination of each component is to determine the first principal component of the current X. This ensures that the starting score (t) is an optimal linear summary of X. This score vector is then orthogonalized against Y to give $t_{new}$. This is done as $$t_{new} = (1 - Y(Y'Y)^{-1}Y')t$$

It can be seen that $t_{new}$ is orthogonal to Y, since:

$$Y' t_{new} = Y'(1 - Y(Y'Y)^{-1}Y')t = (Y' - Y'Y(Y'Y)^{-1}Y')t = 0$$

Thereafter the PLS weights (w) are determined (by an embedded PLS regression) to make t=Xw as close as possible to $t_{new}$. This final estimate of the "orthogonal score vector", t, is then taken a "NIPALS round" through X to give an updated score vector, t, which is then again orthogonalized against Y, and so on until convergence. In this way t is made to converge towards the longest vector that is orthogonal to Y and which still provides a good summary of X.

After convergence, a loading vector, p, is determined, and the residual matrix $E_1$ is then determined by removing from X the orthogonalized scores times the final loadings. This residual matrix is then used as X in the determination of the next "OSC component". The final residual matrix, EA, after the final (A:th) OSC component, constitutes the filtered X-matrix. This filtered X is then, together with Y, for example, used in an ordinary PLS-regression (or principal components regression if one so prefers) to develop the calibration model.

After each component, the normal "projection" diagnostics can be determined, i.e., the model variance of X ($R_x^2$), score plots of to from different components, etc. The latter should, as usual, be checked for outliers since aberrant sample spectra may seriously affect the OSC "model". The "OSC loadings" may provide interesting hints for the causes of the undesired variation.

The resulting OSC-components (a=1,2, ..., A) can now be considered as part of the PLS calibration model. For a new observation (digitized spectrum of a new sample) with the raw data vector $x_{new,raw}'$ (a row vector), predicted values of $y_{new}'$ are demanded (the row vector of responses). Proceeding as follows, just like with an ordinary PLS model, but bearing in mind that the contribution to $y_{new}'$ from the OSC components is zero. First the new x-vector is transformed and scaled in the same way as the training set, giving $x_{new}'$. Then the first score value ($t_{new,1}$) is determined as:

$$t_{new,1} = x_{new}' w_1.$$

The residual vector is then obtained as:

$$e_{new,1}' = x_{new}' - t_{new,1} p_1'.$$

This residual vector is used as the x-vector in the second component, etc., until the corrected $x_{new}$ has been obtained as the residual vector after A OSC components. The corrected x-vector is then used in the calibration model according to the present invention to give predicted values, $Y_{new}'$.

After a presentation in the city of Lahtis, Finland, several chemometricians have proposed that the simplest way to determine an optimal OSC would be to use PCA of the matrix Z, where Z is the X-matrix orthogonalized to Y. Thus each column of Z is:

$$z_k = (1 - Y(Y'Y)^{-1}Y')x_k$$

This determination may work well for a training set, but since no y-values are available for new samples, the x-vectors of these new samples cannot be orthogonalized in the same manner as the training set.

Two OSC components are typically warranted with reflectance NIR spectra, where the first component often resembles a "base-line correction", and the second often to some extent corrects for multiplicative effects. The number of OSC components needed in a given application can be inferred from the amount of X explained in each OSC component. When this is below a value corresponding to an eigen-value of 2.0, i.e., the modelled $R_x^2$ of the component is less than 2/min (N, K), this indicates that more components are not warranted, corresponding to the "eigen-value>1" criterion commonly used in PCA and factor analysis, but made a little safer by using 2.0 instead of 1.0. The orthogonality constraint adds some further rigor to this criterion. More stringent tests for when to terminate an OSC expansion can, of course, be based on cross-validation.

Since OSC with each component removes structure from X that is unrelated to Y, the remainder E will model Y better and better also in the case when X actually contains no significant information about Y at all. Hence OSC with the subsequent PLS (or PCR) analysis converges towards a multiple linear regression (MLR) solution. MLR is known to show a dangerous over-fit with multivariate collinear data, this shows that also OSC-PLS is risky if too many OSC components are allowed.

Hence, the number of OSC components should not exceed a small fraction of min (N, K), thus making the risk small for spurious relations between the corrected X and Y. In the present examples this ratio has been well below 1/10, which seems safe as long as the observations are fairly independent, i.e., not grouped. It is recommend that OSC results are validated with new prediction samples as done in the present examples.

A target rotation method presented by O. M. Kvalheim and T. V. Karstang, Interpretation of latent-variable regression models, Chemometrics and Intelligent Laboratory Systems, 7 (1989) 39–51 and later reviewed by Christie in O. H. J. Christie, Data Laundering by Target Rotation in chemistry-based oil exploration, J. Chemometrics 10 (1996) 453–461 is a filtering method related to PCA and hence also to OSC. This target rotation method uses a specific target score vector to filter the X matrix. The idea with the target rotation is to remove "known" information from X (as expressed by the target vector) that masks the information of interest. But since no orthogonalisation to Y is performed there is a risk for removing information correlated to Y. This problem can be solved by making an orthogonalisation of the target score vector to Y before the target rotation. This will give an orthogonal target rotation method which may provide even better models than the original target rotation method.

Sun recently published a paper using PCA for signal correction, J. Sun, Statistical Analysis of NIR data: Data pretreatment. J. Chemom. 11 (1997)525–532. He found the method useful for removing large base-line variation as well as varying back-ground spectra.

The method of OSC according to the present invention can be seen as an orthogonalized and further modified PCA, which hence should have better properties than the approach of Sun.

Above a direct PLS approach was investigated based on the signal matrix X and a "contrast response matrix" Z=1−Y Y', where Y first has been normalized to unit variance. This gave fairly good results, but the approach is less rigorous than the OSC method according to the present invention.

The results of any projection, including OSC, are influenced by the scaling of the original data in X. In NIR applications one normally either uses unscaled data, data scaled to unit variance (auto-scaling), or something in between these two, e.g., so called Pareto scaling, see S. Wold. PLS for multivariate linear modelling. In QSAR: Chemometric Methods in Molecular Design (Ed. H. van de Waterbeemd), Methods and Principles in Medicinal, S. Wold is the inventor of the present invention.

A problem with scaling of the original data occurs when much of the variation in the X-data is due to light scattering and other phenomena which will be removed by the OSC filtration. Then, the auto-scaling or Pareto scaling will be based on major variation in X that is irrelevant to the actual calibration model.

Hence the use of un-scaled X-data would seem to be more appropriate for OSC-filtering. To circumvent this difficulty, it is possible to run the OSC method on the original (scaled or un-scaled) data and then use the filtered X-matrix to determine a new scaling of the original data, running The OSC method again on the re-scaled X-data.

In this study four different data sets were used for comparison of filtering (signal correction) methods. Three of the data sets are NIR data collected on cellulose derivatives in order to predict the measured viscosity. The fourth data set is NIR data on pulp samples from the pulp and paper industry on which 17 physical properties have been measured.

Each data set is divided into one calibration set and one external test set used for validation of the model predictive ability.

An data set for input to the method according to the present invention was collected at Akzo Nobel, city of Örnsköldsvik, Sweden. The raw material for their cellulose derivative process is delivered to the factory in form of cellulose sheets. Before entering the process the cellulose sheets are controlled by a viscosity measurement, which functions as a steering parameter for that particular batch.

NIR spectra for 181 cellulose sheets were collected after the sheets had been sent through a grinding process. Hence the NIR spectra were measured on the cellulose raw material in powder form. For determination of a calibration model 161 sample spectra were used. The remaining 20 sample spectra were used for model validation.

X: 1201 wavelengths in the VIS-NIR region

Y: Viscosity

N (Calibration set)=161

N (Test set)=20

Another data set contained NIR spectra from 106 cellulose samples in powder form. The XFM cellulose is a raw material in the cellulose derivative process of Akzo Nobel, Örnsköldsvik.

For each of the 106 cellulose samples the viscosity was measured. N=86 sample spectra were used for calibration, while the remaining 20 were used for model validation according to the model of the present invention.

X: 1201 wavelengths in the VIS-NIR region

Y: Viscosity

N (Calibration set)=86

N (Test set)=20

A further data set of Cellulose Sheets were collected at Akzo Nobel, Örnsköldsvik. In this data set the NIR measurements were carried out on the actual cellulose sheets. The measured viscosity for each sheet was used as response variable Y in the model determinations.

NIR spectra for 65 cellulose sheets were collected. N=45 sample spectra were used for calibration and the remaining 20 were used for model validation.

X: 1201 wavelengths in the VIS-NIR region

Y: Viscosity

N (Calibration set)=45

N (Test set)=20

A still further data set was collected at Assi-Domän Corporate Research, the city of Piteå, Sweden. Here NIR spectra for 39 laboratory cooked pulps were collected. For each pulp 17 physical properties were measured. These correspond to product quality parameters commonly used in the pulp and paper industry. The 17 physical properties were used as response variables in the model determinations. N=28 samples were used for the calibration and $N_{valid}$=11 samples were used for the external validation of the model.

X: 233 wavelengths in the VIS-NIR region

Y: 17 physical properties

N (Calibration set)=28

N (Test set)=11

For all the above data sets two OSC components were used for the filtering.

For the cellulose data sets it is clear that the OSC method gives better calibration models, i.e., higher $Q^2$, according to cross-validation (see table 1). Here the $Q^2$-values are defined as $$Q^2 = 1 - PRESS/SSY$$

where PRESS is the predictive sum of squares of the concentration or property matrix Y according to cross-validation, and SSY is the sum of squares of the concentration or property matrix Y around its average vector of the properties. Evaluation of the prediction errors for the external test sets reveals that the OSC treated data provide substantially lower RMSEP values than the raw and MSC data (see table 2). Here RMSEP is the root mean square error of prediction, defined as the square root of the sum of squares of prediction errors divided by the number of elements in this sum, i.e., the variance of the prediction residuals, as further described in the references below for table 3.

Also, the OSC-filtered data give much simpler calibration models with fewer components than the ones based on the raw data (see table 3).

Figure 3A:
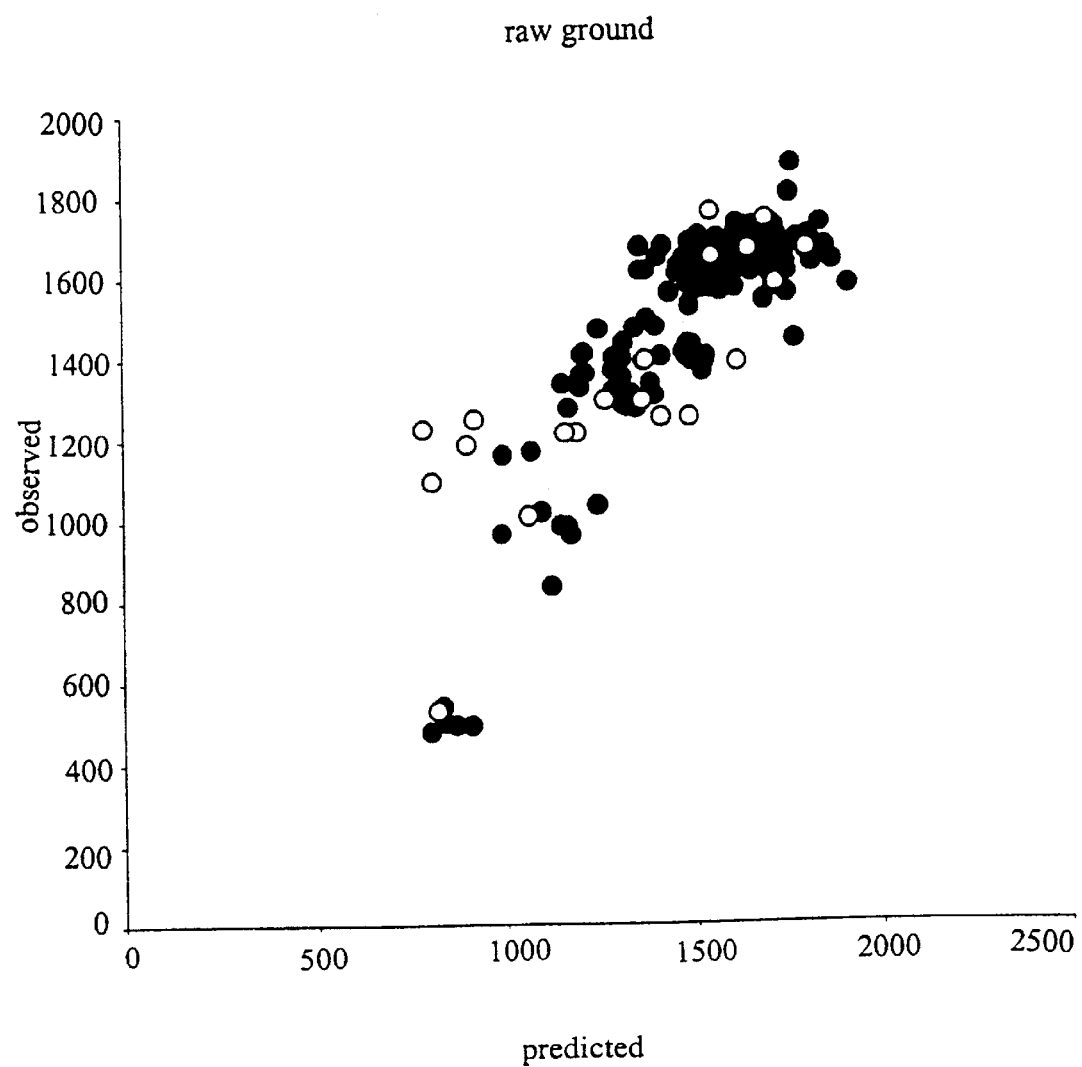
FIGS. 3a, b and c illustrate observed versus predicted viscosity values for PLS models determined from a ground cellulose data set, in FIG. 3a are results from a model based on raw data illustrated, in FIG. 3b results from a model based on MSC filtered data are illustrated, and in FIG. 3c results from a model based on OSC filtered data are illustrated, respectively.
Figure 3B:
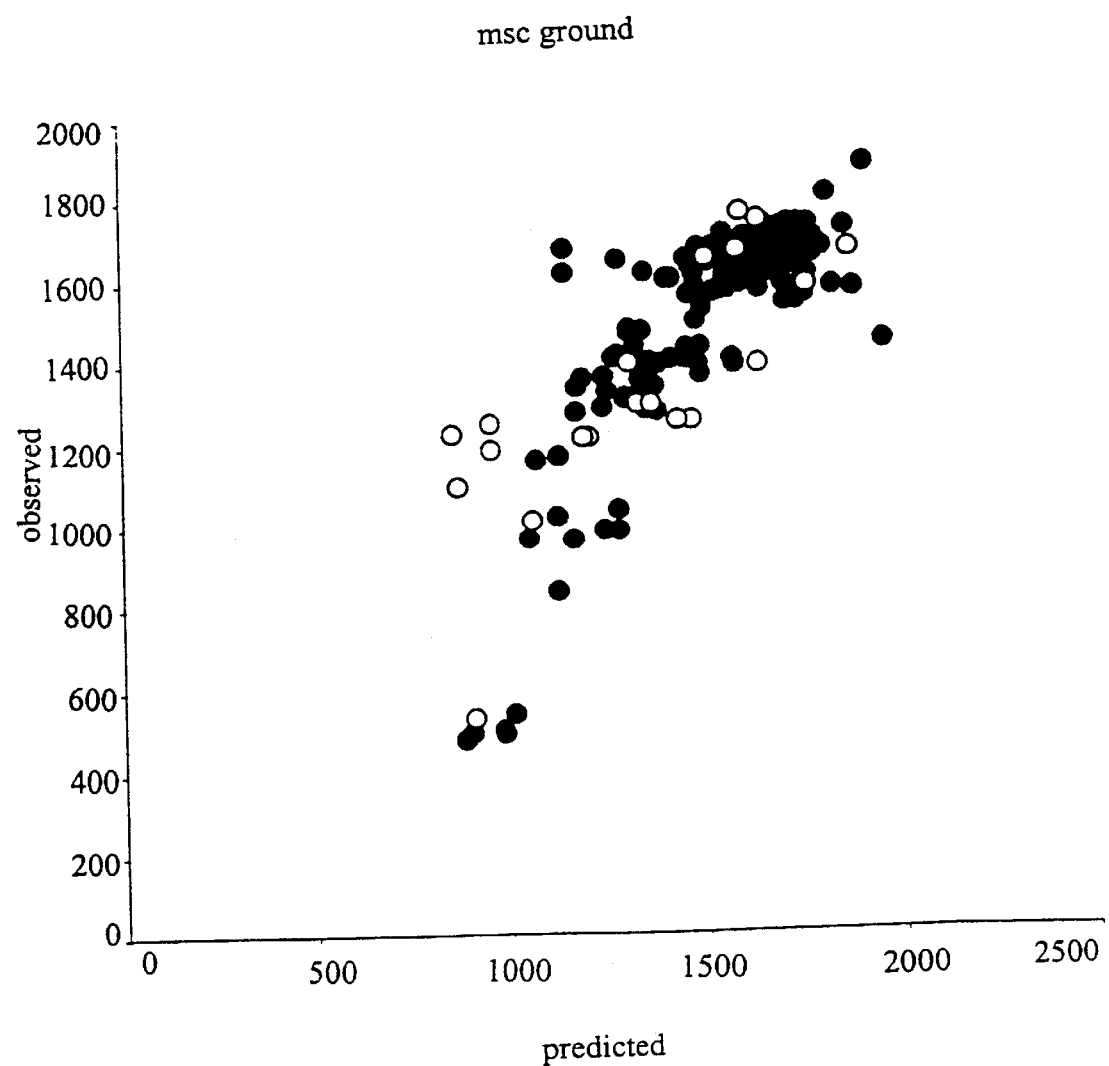
Figure 3C:
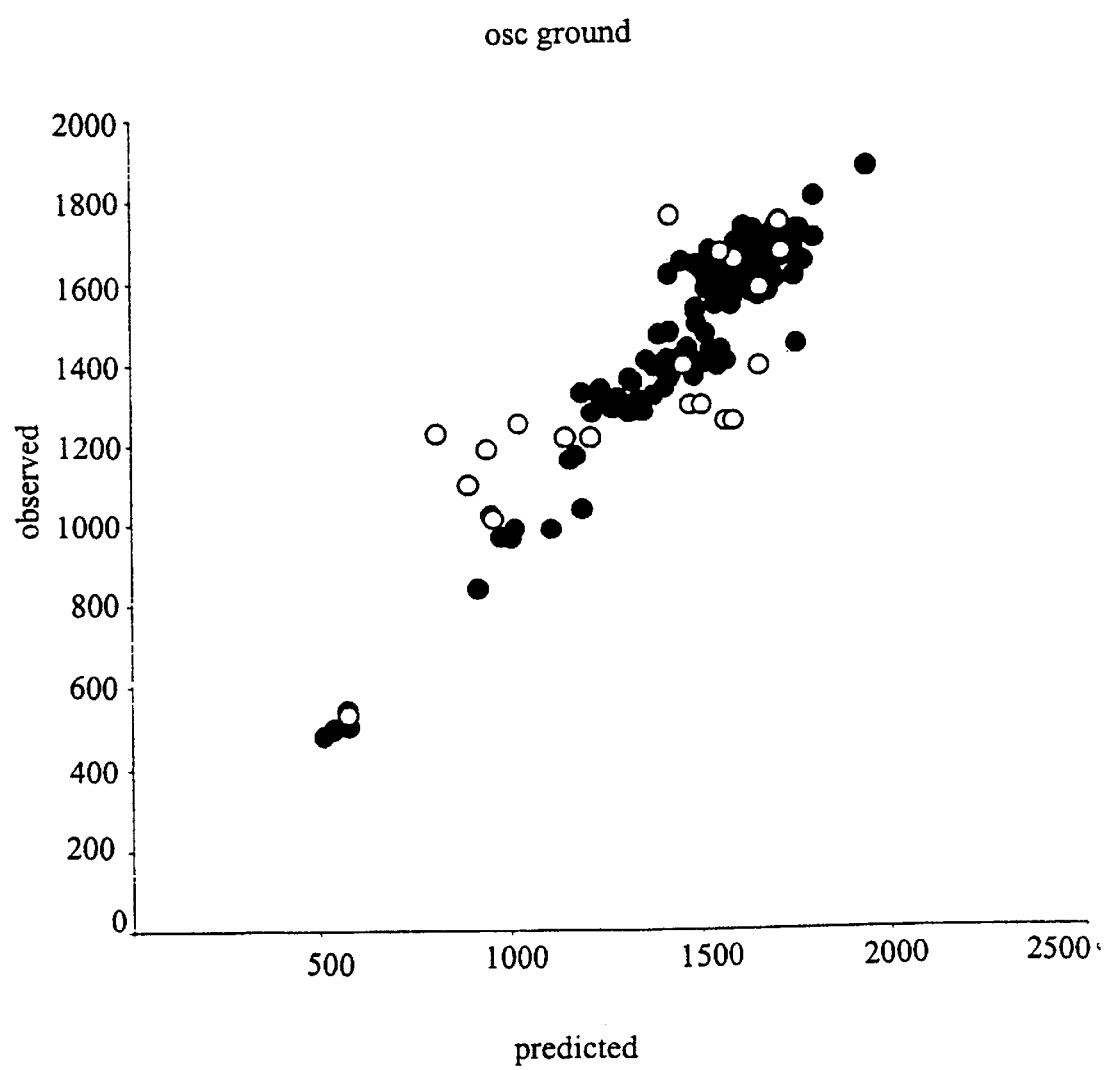

Now, with reference to FIG. 3a–c, which illustrate observed versus predicted viscosity values for PLS models determinated from a ground cellulose data set, in FIG. 3a are results from a model based on raw data illustrated, in FIG. 3b results from a model based on MSC filtered data are illustrated, and in FIG. 3c results from a model based on OSC filtered data are illustrated, respectively.

The observed, open circles, versus predicted, filled in circles, plots in FIG. 3a–c for Y=viscosity, show how the fit and predictions develop from raw data in FIG. 3a via MSC in FIG. 3b to OSC in FIG. 3c, as exemplified by data for ground samples.

For the pulp data set where the Y matrix consists of seventeen measured properties the $Q^2$ values according to cross-validation are about the same for the three calibration models corresponding to unfiltered, MSC-filtered, and OSC filtered data. The RMSEP value for the external test set is, however, lowest for the model determined with OSC treated data.

It is implied by the results that the OSC method indeed removes information from the NIR data that is not necessary for fitting of the Y variables. Since the method gives better predictions of the test set objects, the pre-treatment removes disturbing noise from the NIR data. The results also demonstrate that the OSC method works for models using both single-and multi-Y responses.

Above data reveals that to get good calibration models with low prediction errors some kind of scatter correction is needed. MSC seems to work in many cases but often does not really improve the models significantly. OSC on the other hand for these data sets provides calibration models with substantially better fit and predictive ability.

In some cases the OSC method also removes non-linear relationships between X and Y. This can for example be seen in the observed vs. predicted plots for the data set "Cellulose Ground" (FIGS. 3a to c). It can clearly be seen that the non-linearity in the plots for the raw data and the MSC model while in the plot for the OSC treated data the non-linearity has disappeared.

According to the results shown with the present invention the Orthogonal Signal Correction (OSC) of NIR spectra is a good approach in order to improve multivariate calibration models.

Since evidently projection methods such as PLS are affected by strong systematic variation in the predictor matrix X which is unrelated to the response matrix, Y, there is a need for removing such variation from X before further modelling. Provided by the present invention is a method, where signal correction (filtering) is made in such a way that the removed parts are linearly un-related (orthogonal) to the response matrix Y. OSC has additional advantages beyond improved predictability of the PLS model, such as substantially simpler (fewer components) calibration models, which facilitates the interpretation of the models.

Computationally, the present invention, OSC is based on PLS and the NIPALS method, determining one OSC component at a time. This choice was made because it is proper to implement the orthogonality constraint with, and also to make the method applicable to incomplete data matrixes.

To apply OSC to the filtering of a signal matrix, of course, also a response vector or matrix, Y is needed. This is always present in multivariate calibration applications, but in other cases of filtering it may not be available. In signal analysis, for instance, it is often desirable to filter time series from unwanted noise. Similarly, spectra used for the characterization of materials or products such as pharmaceutical tablets (pills), may look noisy and a filtering would be warranted. When scrutinizing the objective of the characterization, however, it is often possible to construct a "fuzzy" or "soft" response matrix, Y. In time series analysis, for instance, it is possible to use the signals to look for trends—linear or quadratic, or maybe exponential—and then it is possible to construct a Y matrix accordingly with columns varying linearly, quadratically, and exponentially with time.

Analogously, if a spectral matrix from a material characterization is used for classification—e.g., bad materials versus acceptable ones—one may be able to construct an Y-matrix corresponding to this classification.

Other application areas where OSC may be found useful include 3D-QSAR (Three-Dimensional Quantitative Structure—Activity Relationships), where the structures of a set of molecules are translated to a set of structure descriptor vectors by means of, e.g., CoMFA in R. D. Cramer III, D. E. Patterson, and J. D. Bruce. Comparative molecular field analysis (CoMFA). Effect of shape on binding of steroids to carrier proteins. J. Amer. Chem. Soc. 110 (1988) 5959–5967 or GRID in P. J. Goodford, A computational procedure for determining energetically favourable binding sites on biologically important macromolecules. J. Med. Chem. 28 (1985) 849–57. The resulting X matrix which often has thousands of columns but just a few rows, say 15 to 50, is then related by PLS to a matrix Y with measured biological activity values. Since there often is huge parts of X that is unrelated to Y, OSC may help to clean up the data before the analysis, and hence improve the predictivity and interpretability of the solution.

When the number of X-variables, K, is larger than N (the number of training samples), it is always possible to find an exactly orthogonal OSC solution, while if K<N this is not always possible. This also means that for K>N, there are infinitely many OSC solutions, where the method according to the present invention is set up to find the one that models as much of X as possible in each component. This solution may not always be the best, however, and additional constraints on the OSC w vectors may be warranted.

Figure 4:
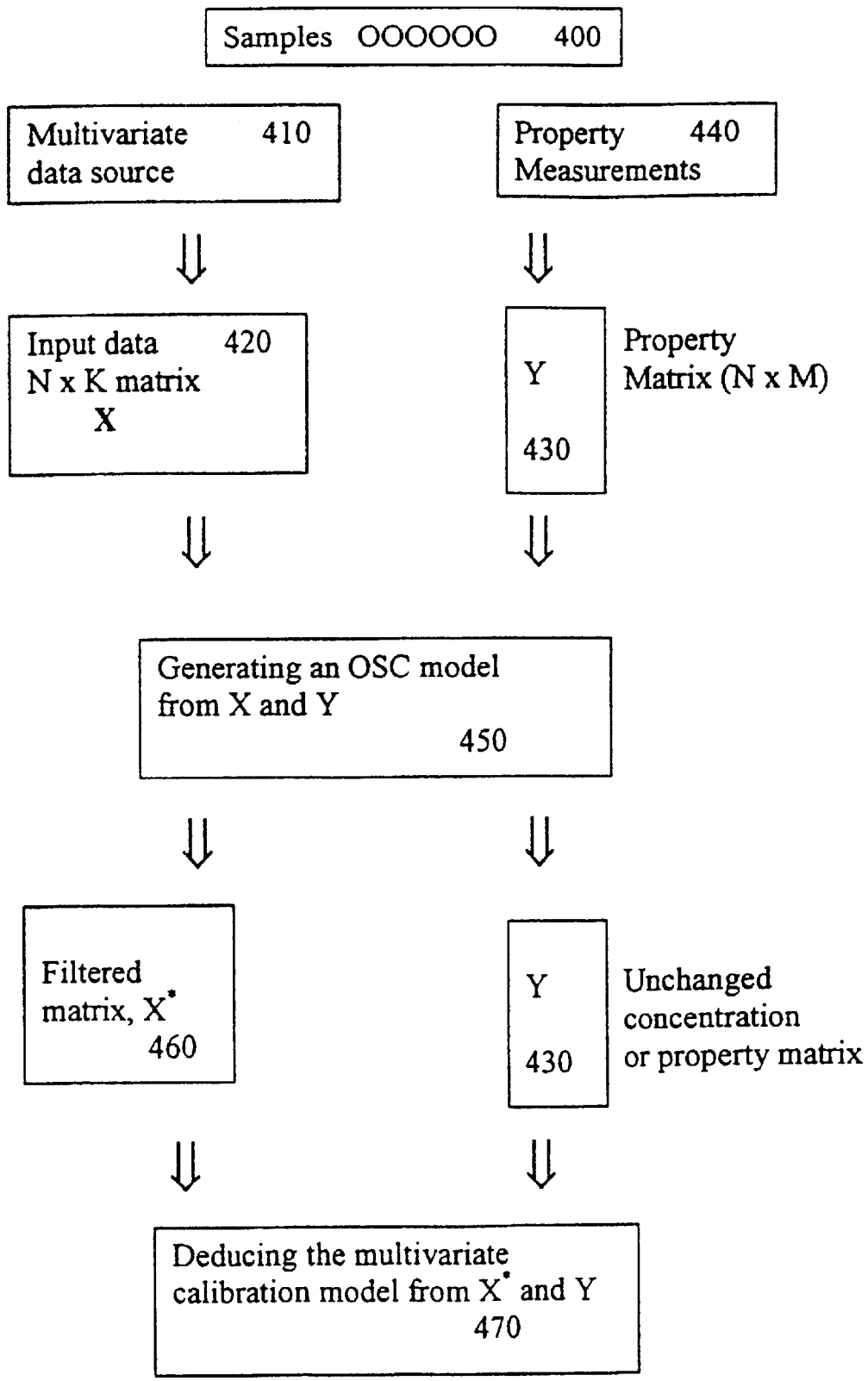
FIG. 4 represents a schematic description of one embodiment of the method according to the present invention.

A schematic description of the method according to the present invention is now provided with reference to FIG. 4.

Samples 400 are taken from a substance or matter and subjected to 410, a multivariate data source, for instance a spectrometer, a chromatograph, or an electrochemical instrument, i.e., an instrument that provides multiple dimensional data, vectors, as a result. The input data is arranged in, for example, a matrix X 420 with N×K elements. The concentration or property matrix or vector Y 430 of size N×M is determined through concentration or property measurements 440 from the sample substance or matter. Hence, according to the above description an OSC 450 model is generated, by employing the X and Y matrixes, and fine tuned with multiple input data samples 400. As a result a filtered X* 460 is created and the Y matrix 430 is kept unchanged. Finally the model 470 is deduced after that a training set of samples has fine tuned the filtered matrix 460 to a multivariate calibration of matrixes X* and Y.

Figure 5:
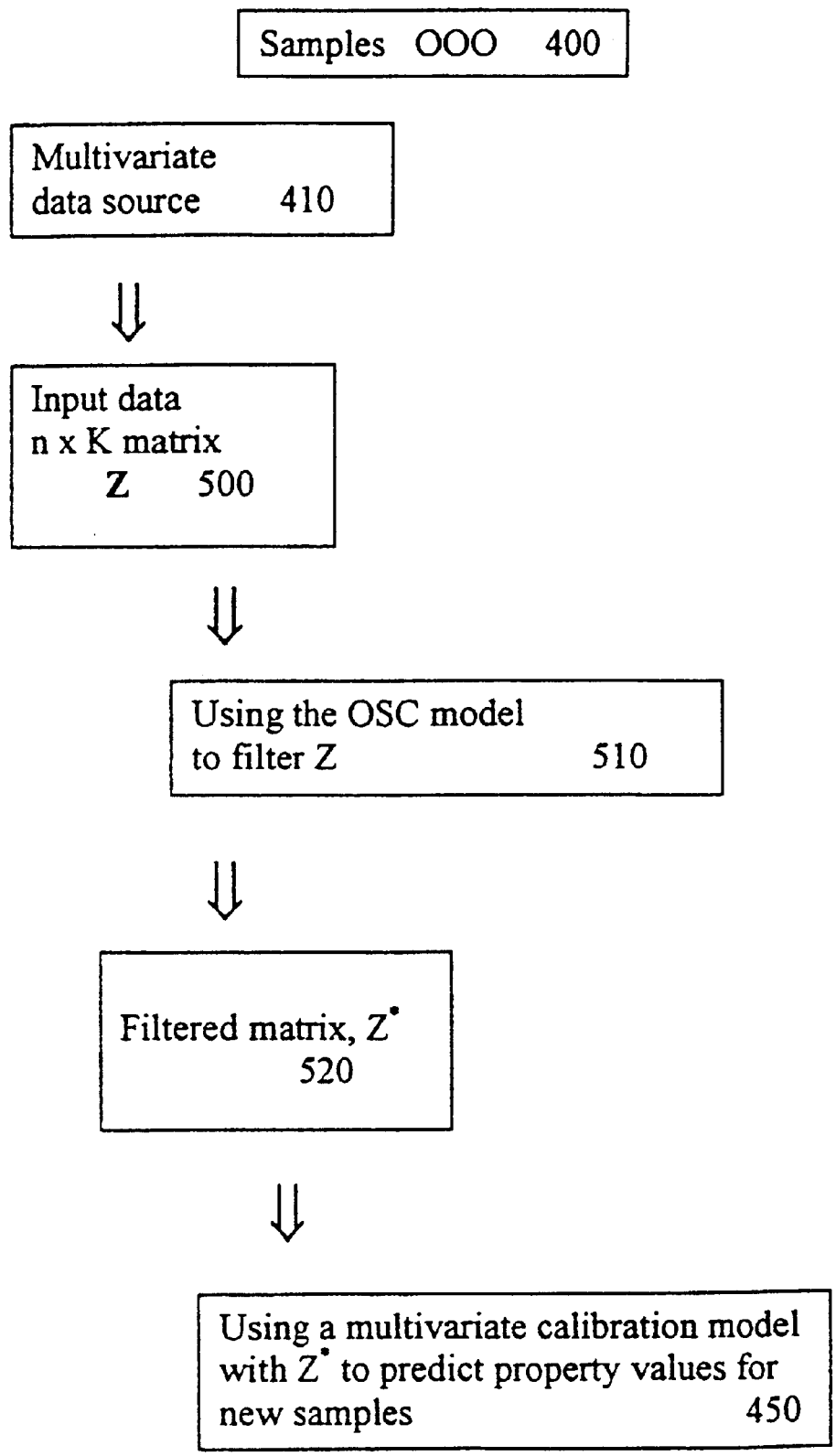
FIG. 5 represents a schematic description of one embodiment of the method according to the present invention.

An example of the multiple training set process comprised in the method, according to FIG. 4 and the method described above, is depicted in FIG. 5. New samples 400 are taken and characterized by the data source 410, giving new input data arranged in a matrix Z 500.

In accordance with the OSC model 450 in FIG. 4, the model 450 is used to filter Z 510 which provides a filtered Z* 520, which is used to determine properties for substances and matter.

Figure 6:
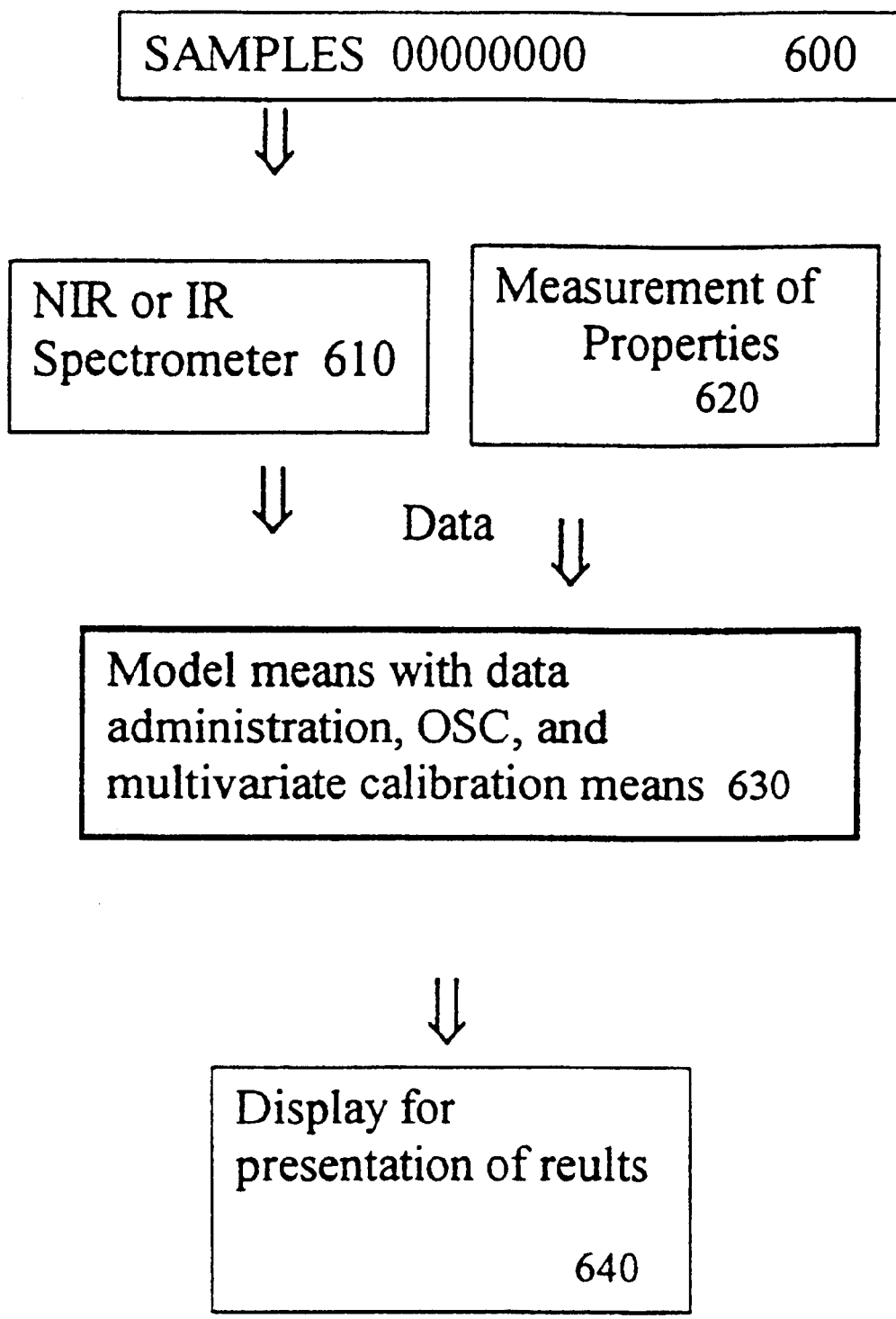
FIG. 6 illustrates an arrangement for concentration or property calibration of samples from a substance or matter from input data relating to spectroscopic data.

Also provided through the present invention, and schematically depicted in FIG. 6, is an arrangement for concentration or property calibration of samples 600 from a substance or matter from input data 610, 620 relating to spectroscopic data.

One preferred embodiment of the arrangement is that concentration or property calibration determines a filter model means 630 for further samples from the same substance or matter, means mentioned below are included in the model 630 schematically depicted in FIG. 6, further comprising the following means:

transforming means, centering means, and scale means to optionally operate on the input data in order to provide two start sets.

arrangement means for arranging sad input data in an input set;

determining means for determining a concentration or property calibration set, a score set and a loading set;

multiplication means for determining the product between the score set and the loading set, said product resembling the spectral set as much as possible under the constraint that score set is orthogonal to the concentration or property set;

filter means for filtering said input data by subtracting said product from the input set in order to remove variations relating to properties other than quality properties; whereby said model determines the filtering model 630, thus providing that further samples, from the same substance or matter, can be filtered with the filter model 630.

Known means for accomplishing the above functions are, for example, spectrometers, chromatographs, filters, drivers (for scaling), multipliers, adders, transformers, computers, software, firmware etc.

The arrangement can thus be used to arrange the sets as two matrixes or one matrix and one concentration or property vector, where the subset is a column of the score matrix.

A filtering according to the present invention is bilinear, but possible to combine with another linear filtering means, such as, for example, wavelet-filtering or Fourier-filtering.

The filter model is preferably improved by applying multiple sets of input data in training sets to said means, thus providing better determined properties by tuning the filtering model.

Results of filtering with the derived model 630 are displayed on displaying means 640.

It is thus believed that the operation and construction of the present invention will be apparent from the foregoing description. While the method and arrangement shown or described has been preferred it will be obvious that various changes and modifications may be made therein without departing from the spirit and scope of the invention as defined in the attached claims.

TABLE 1

$Q^2$-values according to cross-validation for each of the determined models.

|  | Raw | MSC | OSC |
|---|---|---|---|
| Ground | 0.72 | 0.623 | 0.94 |
| XFM | 0.614 | 0.618 | 0.839 |
| Sheets | 0.536 | 0.604 | 0.863 |
| Pulp | 0.54 | 0.54 | 0.57 |

TABLE 2

RMSEP-values for the test set for each of the determined models.

|  | Raw | MSC | OSC |
|---|---|---|---|
| Ground | 199.76 | 195.13 | 183.16 |
| XFM | 616.56 | 478.99 | 428.48 |
| Sheets | 138.55 | 130.54 | 78.43 |
| Pulp | 85.51 | 96.48 | 78.74 |

TABLE 3

Number of PLS components for each of the determined models.

|  | Raw | MSC | OSC |
|---|---|---|---|
| Ground | 5 | 3 | 3 |
| XFM | 3 | 6 | 2 |
| Sheets | 4 | 6 | 1 |
| Pulp | 4 | 4 | 2 |

What is claimed is:

1. A computer-implemented method for concentration or property calibration of input data samples from samples of substances or matter to determine a filter model for further samples of the same substance or matter, comprising:

optionally trnsforming, centermg and scaling the input data;

arranging said input data in an input set matrix X;

determining a concentration or property set matrix Y;

determining a loading set determining with a computer a score set matrix T with a non-standard PLS algorithm having weights w, wherein weights w are defined by the formula:

$$w = X^- t_{new},$$

with $X^-$ representing a generalized inverse of input set matrix X, and w is determined such as to minimize the covariance between matrixes T and Y, which is accomplished by said non-standard PLS algorithm and transforming a score vector t to $t_{new}$ to be orthogonal to said concentration or propety set matrix Y, the product of the loading set and the score set matrix resembling the input set matrix as much as possible under the constrain that the score set matrix is orthogonal to the concentration or property set matrix;

filtering said input data to determine said filter model by subtracting said product from the input set matrix in order to remove variations relating to properties other than present calibration properties;

wherein said filter model provides that further samples, of the same type, can be filtered with the filter model.

2. A method according to claim 1, wherein said input data sets are arranged as two matrixes or one matrix and one concentration of property vector.

3. A method according to claim 1 or 2, wherein said filtering is bilinear and combined with a second linear filtering method.

4. A method according claim 3, wherein said second filtering method is one of wavelet-filtering or Fourier-filteg.

5. A method according to claim 1 wherein said filter model is improved by applying multiple sets of input data as training sets and repeating said steps with a better concentraion or property, thus tuning the filter model.

6. An arragement for concentration or property calibration of spectroscopic input data from samples of substance or matter, to determine a filter means for further spectra of samples of the same type, comprising:

a transforming means, a centering meas, and a scale means to optionally operate on the input data in order to provide two start sets, arrangement means for arranging said input data in an input set matrix X;

determining means for determining, from an input set and a concentration or property calibration set matrix Y, a score set matrix T and a loading set;

calculation means for determining the product between the score set matrix and the loading set, said product resembling the input set matrix as much as possible under the constraint that the score set matrix is orthogonal to the concentration or property set matrix;

filter means for filtering said spectroscopic input data by subtracting said product from the input set matrix in order to remove variations relating to properties other than present calibration properties thereby determining said filter model; whereby said filter model provides that further samples of the same type can be filtered with the filter model and wherein the score set matrix T is determined with a non-standard PLS algorithm having weights w, wherein weigts w are defined by the formula:

$$w = X^- t_{new}$$

with $X^-$ representing a generalized inverse of input ser matrix X and w determined such as to minimize the covariance between matrixes X and Y, which is accomplished by said non-standard PLS algorithm and transforming a score vector t to $t_{new}$ to be orthogonal to said concentration or property set matrix Y, the product of the loading set and the score set matrix resembling, the input set matrix as much as possible under the constraint that the score set matrix is orthogonal to the concentration or property set matrix;

wherein said determining means and calculation means are a computer.

7. An arrangement according to claim 6, wherein said input data sets are arranged as two matrixes or one matrix and one concentration or property vector.

8. An arrangement according to claim 6 or 7, where said filtering means performs bilinear filtering and is combined with a second linear filtering means.

9. An arrangement according to claim 8, wherein said second filtering means is one that provides wavelet-filtering or Fourier-filtering.

10. An arrangement according to claim 6 wherein said filter model is improved by applying multiple sets of input data as training sets, thus providing better determined properties by tuning the filter model.

* * * * *